US00PP32020P2

(12) United States Plant Patent
LaBonte

(10) Patent No.: US PP32,020 P2
(45) Date of Patent: Jul. 28, 2020

(54) SWEETPOTATO PLANT NAMED 'LA17-31'

(50) Latin Name: ***Ipomoea batatas* (L.) Lam.**
Varietal Denomination: LA17-31

(71) Applicant: The Board of Supervisors of Louisiana State University and Agricultural and Mechanical College, Baton Rouge, LA (US)

(72) Inventor: Don R. LaBonte, Baton Rouge, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 16/350,988

(22) Filed: Feb. 8, 2019

(51) Int. Cl.
*A01H 5/06* (2018.01)
*A01H 6/00* (2018.01)

(52) U.S. Cl.
USPC ..... Plt./256

(58) Field of Classification Search
USPC ..... Plt./258, 263.1, 226, 256
CPC ... A01H 5/06; A01H 5/02; A01H 5/12; A01H 5/00; A01H 5/04; A01H 6/00
See application file for complete search history.

*Primary Examiner* — June Hwu
(74) *Attorney, Agent, or Firm* — Baker Donelson

(57) ABSTRACT

A new variety of sweetpotato, identified as 'LA17-31' is disclosed having resistance to southern root-knot nematode and *Fusarium* wilt; an orange flesh, red-purple skin storage root and attractive zero to three or five lobed dark green leaves with purple venation and purple vines.

3 Drawing Sheets

Genus and species name: *Ipomoea batatas* (L.) Lam.
Variety denomination: 'LA17-31'.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

This invention pertains to a new and distinct variety of sweetpotato. This new and distinct sweetpotato variety demonstrates superior disease resistance to *Fusarium* wilt and is highly resistant to southern root-knot nematode, and exhibits storage roots with orange flesh and has ornamental foliage characteristics. It also demonstrates a dark green foliage and zero to three to five lobed leaves in comparison to '05-111' with a lighter color foliage and entire leaf.

This new and distinct sweetpotato variety is characterized by storage roots with orange flesh, consistent shape, a red-purple skin, and dark green foliage.

DETAILED BOTANICAL DESCRIPTION

This new variety of sweetpotato, named 'LA17-31', resulted from an open-pollinated cross performed in 2016 to the female parent 'LA15-538' (not patented). The female parent 'LA15-538' had green palmate leaves. 'LA17-31' was developed to provide a variety with storage root characteristics similar to '05-111' (U.S. Plant Pat. No. 23,761 P3) and attractive foliage for ornamental use.

Plants of 'LA17-31' and variety '05-111' can be differentiated. Leaves of 'LA17-31' are zero to three to five lobed. Most are three to five lobed. '05-111' has an entire leaf with no lobes. Roots of 'LA17-31' are red-purple skin [7.5 R (red) R (purple) (2/8)] and can be differentiated from the light to medium rose skin of '05-111'. Color terminology used herein is in accordance with the MUNSELL® Book of Color (2003 Edition, Munsell Color, GretagMacbeth LLC, 617 Little Britain Road, New Windsor, N.Y. 12553-6148). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'LA17-31'.

'LA17-31' roots were stored during the winter in Chase, La. 'LA17-31' was planted the following spring, resulting in approximately 8-10 sprouts per root. Cuttings from the sprouts were transplanted successfully for asexual reproduction in Chase, La. Asexual propagation of the new cultivar by cuttings has shown that the unique features of this new sweetpotato were stable and that the plant reproduced true to type in successive generations of asexual propagation. Plants described herein were 90 days in age from planting in full sun field plantings.

Figure 1:
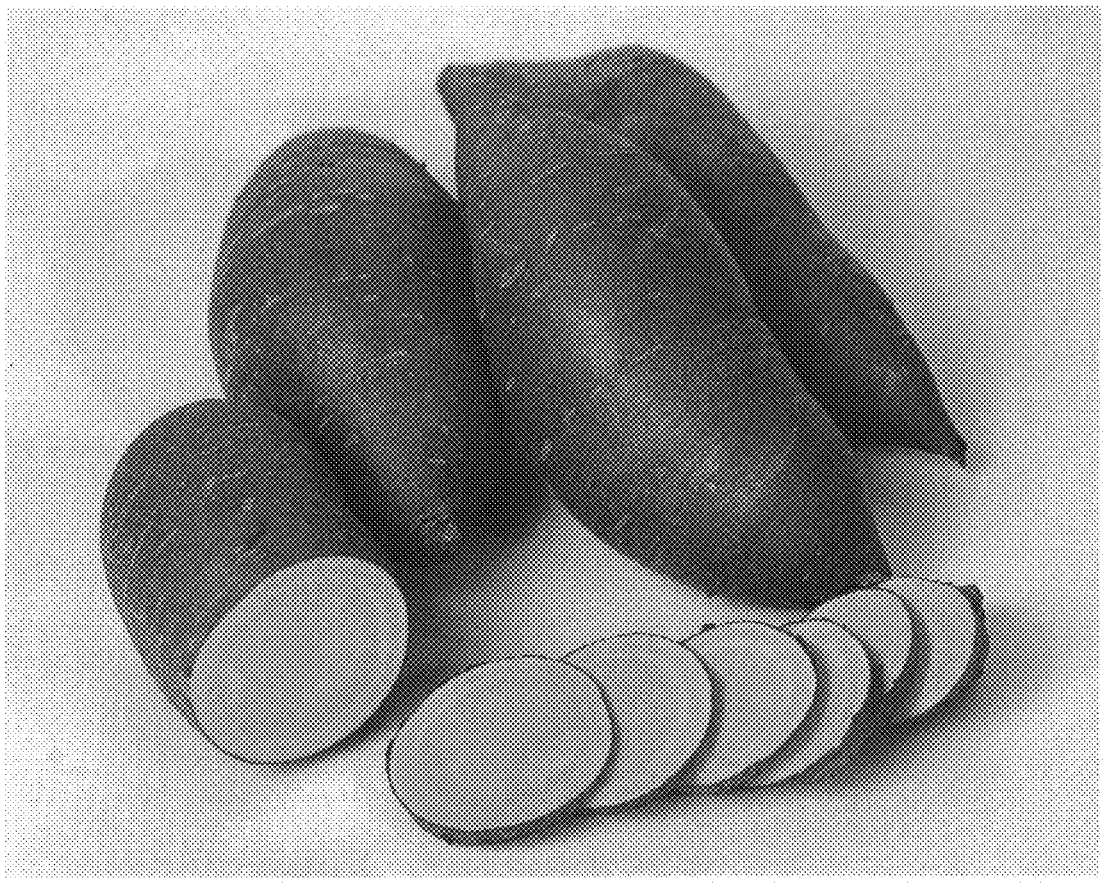
FIG. 1 is a color photograph of the fleshy root form of the novel variety of sweetpotato identified as 'LA17-31'.
Figure 2:
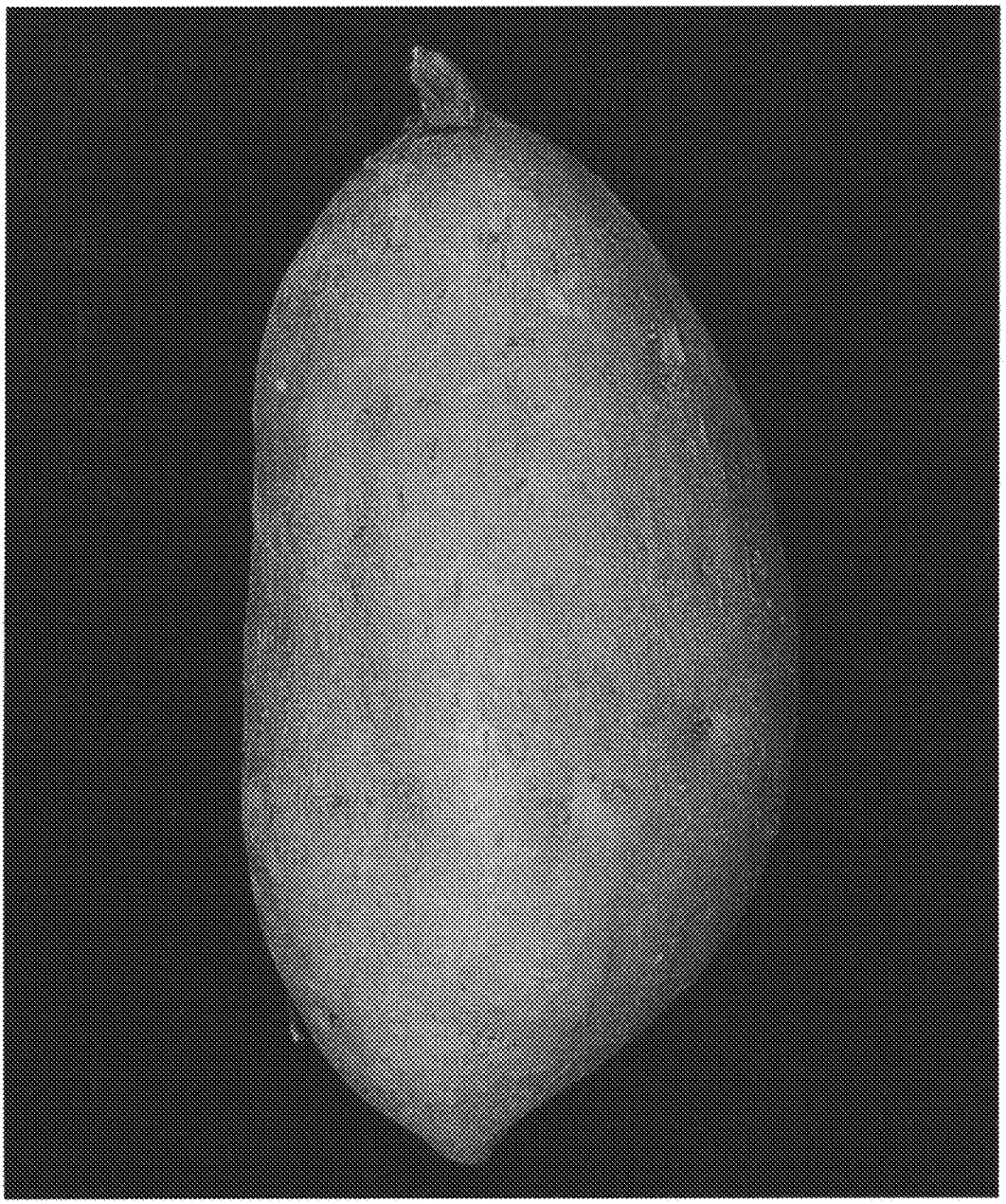
FIG. 2 is a color photograph of the fleshy root form of the sweetpotato variety identified as '05-111'.

FIG. 1 depicts the fleshy root form of the 'LA17-31' sweetpotato. The skin is red-purple and differs from the light to medium rose '05-111', both at harvest and after several months of storage as shown in Table 1. No eyes or longitudinal grooving is present. MUNSELL® Book of Color values for skin and flesh for both 'LA17-31' and '05-111' storage roots are shown in Table 1. The '05-111' sweetpotato is depicted in FIG. 2. The skin for both 'LA17-31' and '05-111' was smooth. The 'LA17-31' cortex was 4.8 mm in depth and the color similar throughout. The flesh of 'LA17-31' is orange and comparable to orange flesh '05-111'.

TABLE 1

| Variable | Variety | Color |
|---|---|---|
| Skin | 'LA17-31' | 7.5 R (red) P (purple) 2/8 |
| | '05-111' | 2.5 Y (yellow) R (red) 6/6 |
| Flesh | 'LA17-31' | 5 Y (yellow) R (red) 6/10 |
| | '05-111' | 2.5 Y (yellow) R (red) 7/8 |

Figure 3:
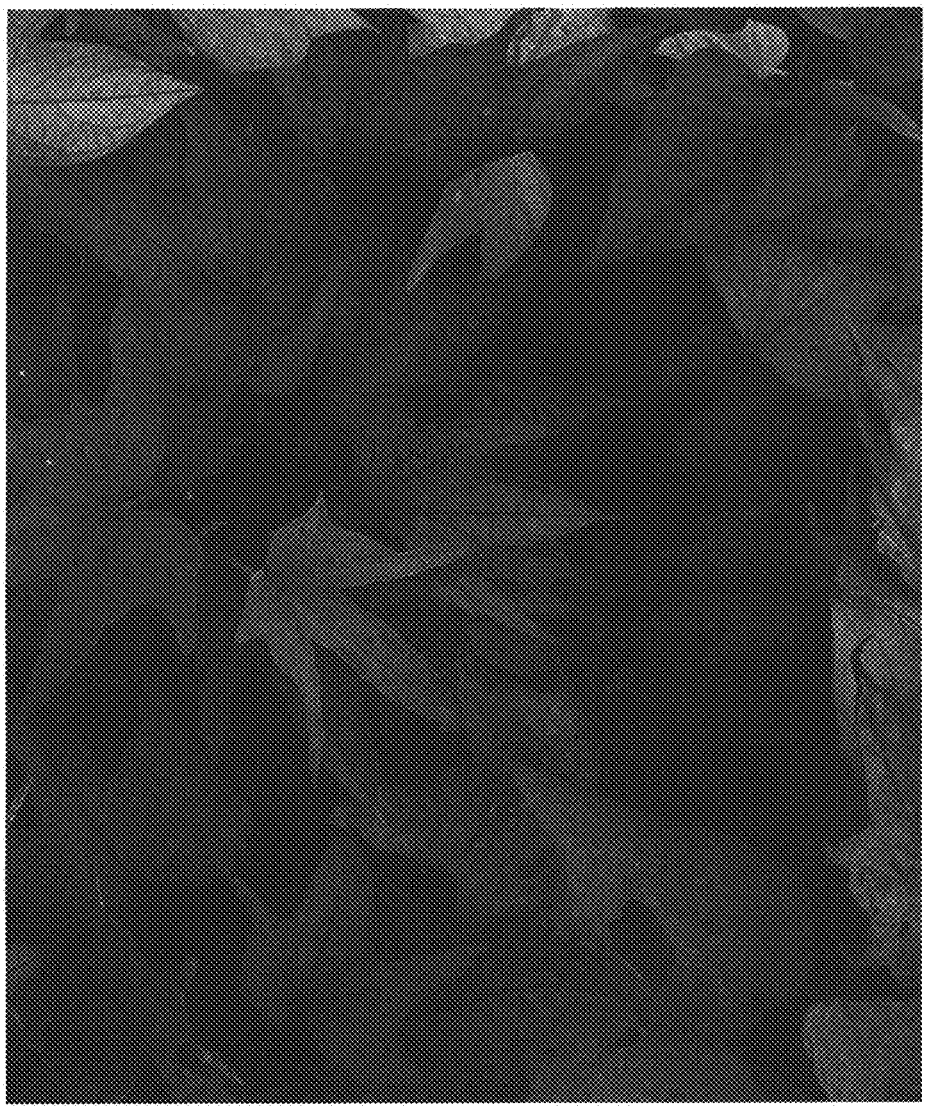
FIG. 3 is a color photograph of the canopy biomass of the novel variety of sweetpotato identified as 'LA17-31'.

FIG. 3 depicts the canopy biomass of 'LA17-31' sweetpotato. 'LA17-31' has round, purple-stemmed vines which change quickly from a green apex [2.5 G (green) Y (yellow) (3/4)] to purple vines [7.5 R (red) P (purple) (2/8)] 3.5 mm from the apex and extends to the crown of the roots. The first 4 cm from the apex is slightly pubescence before becoming glabrous. The 'LA17-31' canopy biomass appears to be similar to '05-111'. The 'LA17-31' canopy architecture was upright and 27 cm in height from the soil surface. For 'LA17-31', four main vines arose from the main stem near the soil surface. The stem giving rise to these vines was 2 cm in diameter; the 4 lateral vines were 98 cm in length with diameters of about 0.9 cm at 65 cm from the base and diameters of about 0.4 cm at the first internode of the first fully developed leaf from the apex. The spread is compact compared to '05-111'. Four lateral branches arose from each of the main vines. At the first internode from the apex, the internode length was about 1.2 cm between the first and second fully developed leaves. Internode lengths for other sections of the vine averaged about 8 cm. Unfolded immature leaves were green [2.5 G (green) Y (yellow) (5/4)] for the adaxial and abaxial surface, which change over one node from the apex. The open leaves turn to a dark green [2.5 G (green) Y (yellow) (3/2)] and the abaxial surface takes on a slight purple hue [2.5 P (purple) (4/2)]. The stem tip anthocyanin coloration is absent, and pubescence is absent. Mature leaves five nodes from the apex had an acute apex and mostly a cordate base and medium 3 or 5 lobed lamina. A few leaves are shallow lobed. Leaf margins are entire. Mature leaves were about 9.6 cm long and 13.2 cm wide. The abaxial and adaxial leaf surface is smooth. Adaxial and abaxial veins were in a pinnate venation pattern with medium extent of purple [7.5 R (red) P (purple) (2/4)] coloration. The petiole was purple [7.5 R (red) P (purple) (2/4)]. The coloration extended from the leaf veins to the petiole in a continuous fashion. The petiole was 13.5 cm long at five nodes from the apex, and 2.5 mm in diameter at 5 cm from the leaf junction. The dormant nodal meristem was purple [7.5 R (red) P (purple) (2/8)].

A typical inflorescence of 'LA17-31' displayed two clusters of 4-5 flowers per peduncle. Peduncles were purple [7.5 R (red) P (purple) (2/4)], about 6-8 cm long, and about 3 mm in diameter. Individual flowers were about 3 cm long from the base of the calyx, and the corolla was 3 cm wide at the opening. The fused flower petals formed a pentagonal pattern with smooth edges. The inner throat of the corolla was purple [7.5 P (purple) (3/8)]. The inner and outer limbs of the corolla (corollas outermost area, distal from the calyx) were light purple [10 P (purple) (9/2)]. The five sepals comprising the calyx were elliptic with a cordate apex and green [2.5 G (green) Y (yellow) (5/4)] along the margins and mostly purple [7.5 P (purple) (4/6)]; three of these sepals were about 11.8 mm long and 5.0 mm wide. Two other sepals (interspersed) were about 9 mm long and 2.4 mm wide. Sepal margins were entire. Stigmata were about 1.0 cm long and light purple [10 P (purple) (9/2)] at the base before fading. Five stamens were inferior to the stigmata. There were small flag like tissue attached to stamen bases and similar in color to the outer corolla. A slight sweet fragrance was present. Mature seed capsules are round and 6.0 mm in length and width, and seeds are 3.5 mm round. One black [neutral 1.75] seed is produced on average per capsule.

EXAMPLE 1

Tests Conducted

To confirm that 'LA17-31' was a new ornamental variety with storage roots, controlled tests (e.g., pathogen responses and yield) were conducted in Baton Rouge, La. '05-111' was selected for comparison because of its importance in commercial United States orange flesh sweetpotato acreage. Diseases that commonly affect the growth of sweetpotatoes were selected to test for pathogen responses in both varieties. 'LA17-31' and '05-111' were resistant to *Fusarium* wilt or stem rot caused by *Fusarium oxysporum* Schlect. f sp. *batatas* (Wollenw.) Snyd. & Hans. 'LA17-31' was susceptible and '05-111' was intermediate to resistant for *Streptomyces* soil rot caused by *Streptomyces ipomoeae* (Person & W. J. Martin) Waksman & Henrici.

Nematode reproduction was measured in greenhouse tests. 'LA17-31' was highly resistant while '05-111' was susceptible to race 3 of the southern root-knot nematode, *Meloidogyne incognita* (Kofoid & White 1919) Chitwood 1949.

Storage roots have a storage life similar to '05-111'. There are no data on shipping or storage root market use.

'LA17-31' is drought and heat tolerant like '05-111' and succumbs to death at freezing like '05-111'.

'LA17-31' has not been tested for novel insect resistance.

To determine yield production, complete-block trials using three replications of 'LA17-31' and '05-111' were conducted in 2018 in Louisiana and Arkansas. 'LA17-31' and '05-111' sweetpotato plants were transplanted in randomized complete-block trials at 31-cm spacings. Each block/plot was fertilized with approximately 250 pounds per acre of a mixed fertilizer comprising 13% N, 13% $P_2O_5$, and 13% $K_2O$. 'LA17-31' was compared to '05-111' at transplanting dates in June. Average yields were measured for the following grades of roots: U.S. #1 (51-89 mm in diameter, 76-229 mm long); Canner (25-51 mm in diameter, 51-178 mm long); and Jumbo (larger than U.S. #1 in diameter, length or both, and without objectionable defects). A typical marketable root of 'LA17-31' was 180-190 mm long, 60-70 mm in diameter, with mostly round-elliptic in shapes. The base or distal end tended to be more elongated in comparison to slightly rounder apex (proximal end). U.S. #1 roots typically weighed 150-190 g.

A mid-season transplanting date trial was conducted at Gilbert, La. in 2018. 'LA17-31' and '05-111' were transplanted on Jun. 19, 2018 and harvested on Oct. 19, 2018 (123 days after planting). Average yields, measured as Metric Tons per Hectare ($MT \cdot ha^{-1}$), are shown for 'LA17-31' and '05-111' in Table 2.

TABLE 2

Mid-season transplant date yield trial.

| Selection | US #1[†] | Canners[†] | Jumbos[†] | TMY[‡†] |
|---|---|---|---|---|
| 'LA17-31' | 10.25a | 10.25a | 0.00a | 20.51a |
| '05-111' | 10.98a | 11.23a | 0.00a | 22.21a |

[†]Average yields in $MT \cdot ha^{-1}$ of varieties followed by a common letter do not differ significantly ($P < 0.05$) according to Duncan's Multiple Range Test.
TMV[‡] = total marketable yield A mid-season transplanting date trial was also conducted at Wynne, Ark. in 2018. 'LA17-31' and '05-111' were transplanted on Jun. 5, 2018 and harvested on Oct. 9, 2018 (127 days after planting). Average yields, measured as Metric Tons per Hectare ($MT \cdot ha^{-1}$), are shown for 'LA17-31' and '05-111' in Table 3.

TABLE 3

Mid-season transplant date yield trial.

| Selection | US #1[†] | Canners[†] | Jumbos[†] | TMY[‡†] |
|---|---|---|---|---|
| 'LA17-31' | 24.26a | 13.87a | 6.56a | 44.71a |
| '05-111' | 16.5a | 11.04a | 8.74a | 36.25a |

[†]Average yields in $MT \cdot ha^{-1}$ of varieties followed by a common letter do not differ significantly ($P < 0.05$) according to Duncan's Multiple Range Test.
TMV[‡] = total marketable yield As shown in Tables 2-3, 'LA17-31' was competitive in yield in comparison to '05-111' in regional trials at various planting dates. 'LA17-31' had harvestable roots approximately 120-130 days after planting, which is typical development time for sweetpotatoes and comparable to '05-111'. 'LA17-31' is not intended for commercial production but demonstrates competitive yield in comparison to a commercial orange flesh fresh market variety.

'LA17-31' should be a valuable commercial ornamental sweetpotato variety. 'LA17-31' has competitive yield in comparison to '05-111' and represents a unique canopy type which produces edible red-purple skin, orange flesh roots.

What is claimed is:

1. A new and distinct variety of *Ipomoea batatas* plant named 'LA17-31' as described and illustrated in the specification herein.

* * * * *